United States Patent [19]

Greenwood

[11] Patent Number: 4,922,612
[45] Date of Patent: May 8, 1990

[54] OSCILLATORY SAW

[75] Inventor: Eugene C. Greenwood, Costa Mesa, Calif.

[73] Assignee: Henry E. Bruce, Mission Viejo, Calif.

[21] Appl. No.: 207,728

[22] Filed: Jun. 16, 1988

[51] Int. Cl.[5] ............................................. B23D 45/16
[52] U.S. Cl. ...................................... 30/166.3; 74/25; 606/178
[58] Field of Search ............... 30/388, 392, 166, 394; 74/25; 128/317

[56] References Cited

U.S. PATENT DOCUMENTS

| | | | |
|---|---|---|---|
| 2,427,580 | 9/1947 | Stryker | 30/166 |
| 2,557,364 | 6/1951 | Treace | 128/317 |
| 3,044,171 | 7/1962 | Cecere | 30/166 |
| 3,103,069 | 9/1963 | Gary | 30/124 |
| 3,952,412 | 4/1976 | Rhodes | 30/166 |
| 4,229,963 | 10/1980 | Savinov et al. | 74/25 X |
| 4,252,121 | 2/1981 | Arnegger | 128/317 |

*Primary Examiner*—Frank T. Yost
*Assistant Examiner*—Willmon Fridie, Jr.
*Attorney, Agent, or Firm*—Price, Gess & Ubell

[57] ABSTRACT

A high speed short stroke saw for cutting plaster casts, bone and the like, is constructed to operate with minimal noise from the mechanism. The motor driven rotary shaft and the oscillating saw blade shaft are mounted in bearing support structures in a casing. The rotary motion of the motor shaft is translated to the oscillating motor of the saw blade by a bearing mounted cam that fits within a drive rod and receives the motor shaft. The drive rod is connected to a bearing mounted crank which receives the saw blade shaft. This entire mechanism is sealed in oil.

10 Claims, 2 Drawing Sheets

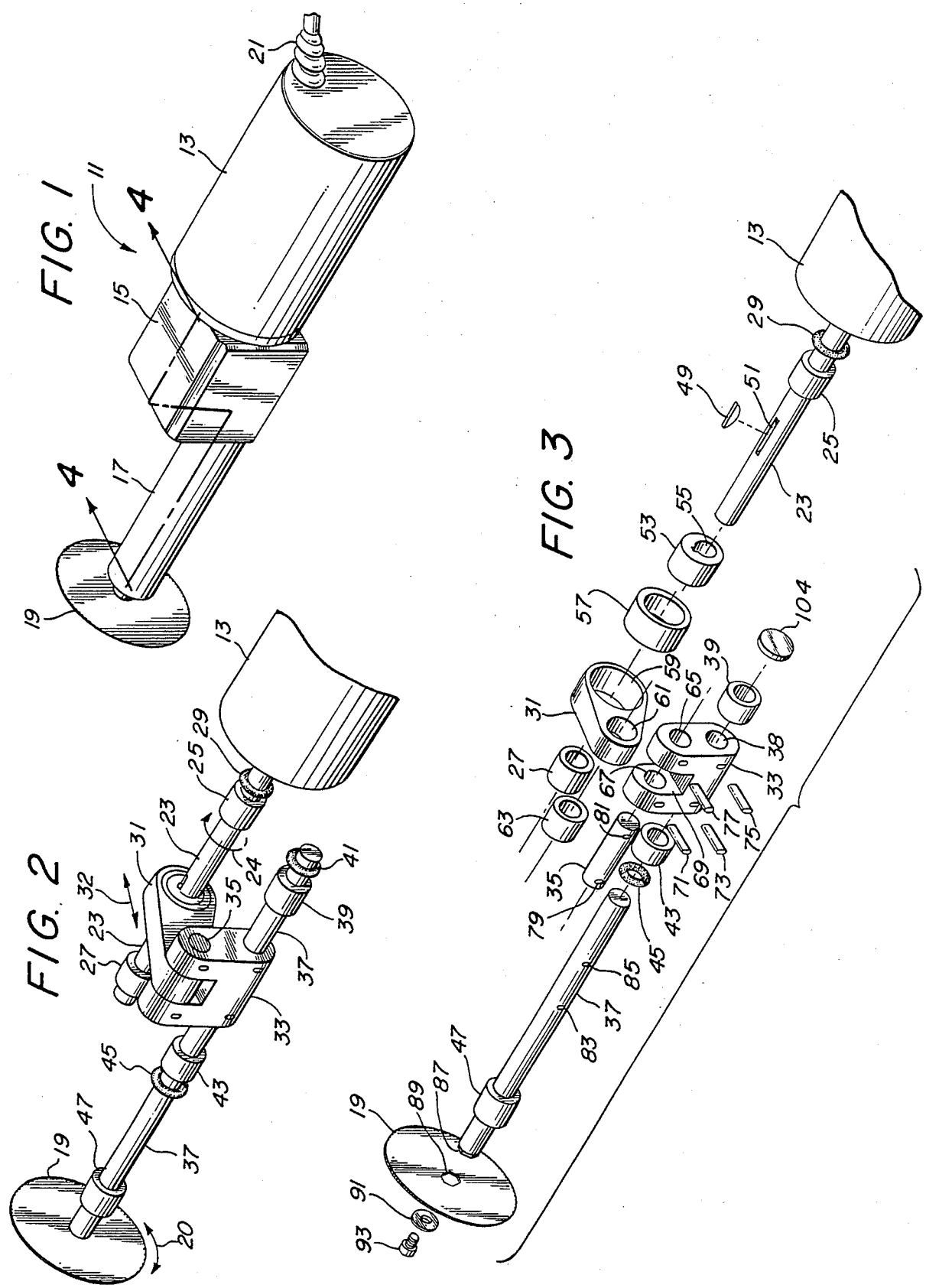

OSCILLATORY SAW

BACKGROUND OF THE INVENTION

1. Field of the Invention

The present invention relates generally to improvements in saws, and more particularly, pertains to new and improved oscillatory saws of the type used for cutting plaster casts, bone and the like.

2. Description of the Prior Art

In the field of oscillatory saws, it has been the practice to employ an oscillating mechanism to convert rotary motion to the oscillatory motion of the cutting blade of the saw. These devices although functioning satisfactorily have been unsatisfactory in that they make a continuous loud and frightening sound when operating. This sound is present without any sawing activity. The sound tends to terrify children and causes even strong adults to have moments of panic. The blade of a cast-cutting saw is typically a thin blade of steel two inches in diameter with saw teeth on the periphery. It differs from an ordinary radial saw in that the blade does not rotate. Instead the blade simply oscillates. It moves a short distance in the clockwise direction then reverses and goes a similar distance in a counterclockwise direction. A typical distance of movement is 0.05 inches on the periphery. However, this can vary. The purpose of the oscillating movement is so that the blade will not cut skin. As it touches skin, which is resilient, the skin moves back and forth with the saw teeth without being cut or ruptured. However, when coming into contact with cast material, which is hard and brittle, the blade cuts and breaks away the cast material as the blade oscillates against it. This is also true when the blade oscillates against bone material.

The oscillating mechanism used by the prior art causes the loud noise made by the prior art saws. Typical arrangements involve a motor rotating a ball bearing mounted on an eccentric shaft which moves within a metal fork, knocking it first in one direction and then in the other. The saw blade shaft is pinned at the other end of the fork and is oscillated back and forth. This kind of structure is illustrated in U.S. Pat. Nos. 2,427,580 and 4,252,121.

Other oscillatory saw structures which utilize cams and cam followers are illustrated in U.S. Pat. Nos. 3,044,171 and 3,952,412.

SUMMARY OF THE INVENTION

According to the present invention, the general objects and an oscillatory saw that is virtually silent is attained by eliminating the fork-type mechanism and by having the rotary to oscillating motion conversion mechanism sealed in a casing and in oil. Both the rotary motor shaft and the oscillating saw blade shaft are supported in bearing structures in the casing. A bearing mounted cam in a drive rod receives the rotary shaft. The drive rod is connected to a crank through a bearing surface. The crank receives the saw blade shaft. Since all moving parts are in continuous contact, no impact sound is created.

BRIEF DESCRIPTION OF THE DRAWINGS

The exact nature of this invention and many of the attendant advantages will be readily appreciated as the same becomes better understood by reference to the following detailed description when considered in conjunction with the accompanying drawings in which like reference numerals designate like parts throughout the figures thereof and wherein:

FIG. 1 is a three-dimensional perspective assembly of the preferred embodiment of the present invention;

FIG. 2 is a three-dimensional assembly of the preferred embodiment of the present invention shown in FIG. 1 with the casing removed;

FIG. 3 is a blow-up illustrating the linkage mechanism of FIG. 2;

DESCRIPTION OF THE PREFERRED EMBODIMENTS

Figure 4:
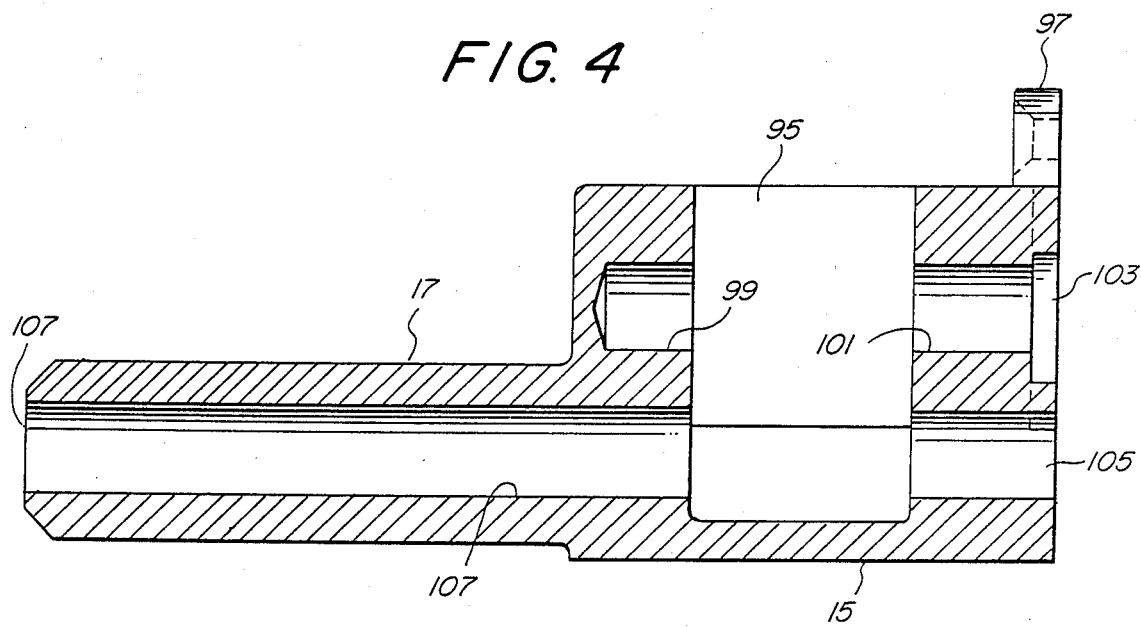
FIG. 4 is a section of the casing shown in FIG. 1.
Figure 5:
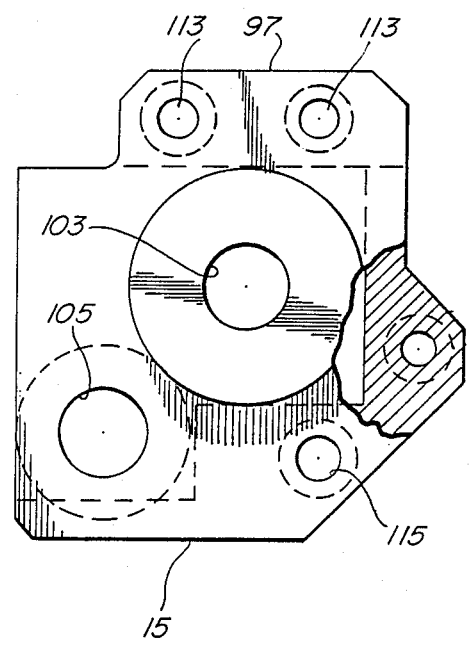
FIG. 5 is an end view of the casing of FIG. 1.

The oscillatory saw 11 according to the present invention utilizes a motor 13 which drives a cutting blade 19 in an oscillatory fashion. The motor 13 for the purposes of this invention is preferably a DC motor which is compact and quiet. However, the invention should not be considered as so limited since any form of compact, quiet motor means is contemplated hereby. The motor 13 drives the saw blade 19 through a linkage system contained within casing 15 and casing extension 17.

Although FIG. 1 illustrates the invention as being essentially a single unit with the motor 13 as part of that unit being fed by power connector cables 21, it should also be understood that the remote location of motor 13 is also contemplated whereby rotary motion may be supplied to casing 15 over a cable mechanism (not shown) from a motor that may be located in another room, for example.

Contained within casing 15, 17 is the linkage mechanism that turns the rotary motion 24 of shaft 23 into oscillatory motion 20 of blade 19 perpendicular to shaft 37. Shaft 23 is supported in casing 15 by a pair of bearings 25 and 27. Shaft 23 engages a drive rod 31 through a cam and bearing mechanism (FIG. 3) which will be described below. Drive rod 31, as a result of the rotary motion 24 of shaft 23, moves back and forth in direction 32. Drive rod 31 is connected by a connecting shaft 35 to crank 33 causing the crank 33 to move with drive rod 31. Crank 33 is pinned to oscillating shaft 37. Oscillating shaft 37 is supported in the casing 15, 17 by a plurality of bearing structures 39, 43 and 47. Accordingly, as crank 33 is moved back and forth in direction 32, it causes quick oscillatory motion of the saw blade 19 in the arcuate direction 20. It is this oscillatory motion 20 of the cutting blade 19 which easily cuts through hard, brittle material such as a plaster or fiberglass cast or bone, but causes no injury to resilient, movable material such as skin.

The rotary to oscillatory motion conversion mechanism illustrated in FIG. 2 provides the desired noiseless operation of the mechanism. The preferred structure for accomplishing this end is illustrated in FIG. 3. The rotary drive shaft 23 has a slot 51 located therein which receives a key 49. The circulatory cam 53 having an offset keyhole 55 therein slips over rotary drive shaft 23 and locks into place for fixed rotation with shaft 23. It is locked into place by key 49. The circular cam 53 rotatably fits within bearing 57, which is press fit within aperture 59 of drive rod 31. The outboard end of rotary shaft 23 is supported by a bearing 27. The inboard end of shaft 23 is supported by a rotary bearing 25.

Drive rod 31 contains a small aperture 61 therein at its small end. A rotary bearing 63 is located within this aperture. Bearing 63 receives connecting shaft 35 when the smaller end and aperture 61 are placed within slot opening 69 of crank 33. When so placed, the connecting shaft 35 slides through apertures 67 and 65 of crank 33 and through bearing 63 to connect the small end of drive rod 31 to crank 33. A pair of pins 71 and 77 are driven through apertures in crank 33 and apertures 79, 81, respectively, in connecting shaft 35, thereby fixedly pinning connecting 35 to the crank 33. When movement occurs between drive rod 31 and crank 33, movement will be between the inner surface of bearing 63 and connecting shaft 35.

The oscillatory shaft 37 is pinned to crank 33 by a pair of pins 73, 75. Shaft 37 is placed through aperture 38 at the bottom end of crank 33 so that holes 83, 85 line up with mating holes in the crank block 33. Pins 73, 75 are then driven through the holes pinning the saw shaft 37 to the bottom half of crank 33. Bearing 39 supports one end of shaft 37. Bearing 43 supports the middle part of shaft 37. Bearing 47 supports the saw blade end of shaft 37. Closure plug 104 simply closes the opening on the casing 15, as shown in FIG. 4.

The blade end of shaft 37 has a hex or some other shaped nut on its end which engages a mating cutout 89 on the blade thereby fixedly attaching blade 19 to shaft 37 when bolt 93 and washer 91 hold blade 19 fast to the threaded hex insert 87.

A plurality of 0-ring seals 29, 41 and 45, for example, are utilized for the purpose of sealing fluid in the casing 15, 17. When assembled in the casing, the motion translation mechanism is completely contained in a lubricating fluid such as a lubricating motor oil of an appropriate viscosity.

FIG. 4 illustrates the cross-section of a casing shown in FIG. 1 having a main portion 15 and an extended portion 17. Extended portion 17 has a bore 107 therein through which the oscillating shaft 37 passes and extends outward from the casing at aperture 109. The bore 107 extends through the extended portion of casing 17 entering into a major chamber 95 within which is contained the major translational mechanisms such as the drive rod 31, the crank 33, and the associated cams, connecting pins and bearings. The closure tab 104 (FIG. 3) fits into aperture 105 to seal the casing. The bore 107 is sized to accept bearings 47, 43 and 39 in a press-fit relationship thereby holding the oscillatory saw shaft 37 in the preferred alignment.

The rotary shaft 23 fits within bore 99 and 101 on either side of major chamber 95. Bearings 27 and 25 respectively press-fit into bore 99 and 101 as drive shaft 23 passes through aperture 103 into bore 101 and 99. O-ring seal 29 seals in the lubricating fluid at all times, even during the rotation of shaft 23.

The casing 15, 17 may attach to the motor mechanism by a flange 97 having a pair of apertures 113, therethrough for threaded bolts (not shown). In addition, another aperture 115 may be located at the lower end thereof for another fastening bolt.

The oscillatory saw operates as follows. As the motor 13 rotates, the rotary shaft 23 turns cam 53 which in turn causes drive rod 31 to move back and forth. Drive rod 31 thereby pushes crank 33 in one direction and then pulls it back again. The other end of crank 33 consequently oscillates the oscillatory shaft 37, first in one direction and then the other. During this motion, rotary shaft 23 and oscillatory shaft 37 are kept in parallel relationship by the respective bearings 25, 27 and 39, 43 and 47, which are mounted in casing 15, 17. The interior of the casing retains a supply of lubricating fluid which is present to lubricate all the moving parts including all the bearings therein. The result of all the moving parts moving within bearings and being fully sealed and lubricated is a virtually silent operation.

What is claimed is:

1. A high speed, short-stroke oscillatory saw for cutting plaster casts or bone, and the like, comprising:
    a casting filled with a lubricating fluid;
    a rotary shaft mounted for rotation within said casing;
    a cylindrical cam fixedly attached to said rotary shaft for rotation therewith;
    an oscillatory shaft mounted for circumferential oscillating motion within said casing;
    a crank fixedly attached to said oscillatory shaft for movement therewith; and
    a drive rod having a first cylindrical bearing surface therein for receiving said cylindrical cam for rotation therewith and imparting an oscillatory motion to said crank.

2. The oscillatory saw of claim 1 wherein said drive rod has a second cylindrical bearing surface thereon, and further comprising:
    a connecting shaft rotatably located within said second cylindrical bearing surface of said drive rod and fixedly attached to said crank for connecting said drive rod and said crank.

3. The oscillatory saw of claim 2 wherein said casing is sealed and filled with a lubricating fluid.

4. The oscillatory saw of claim 1 further comprising at least one bearing surface in said casing for rotatably receiving said rotary shaft.

5. The oscillatory saw of claim 4 further comprising at least one bearing surface in said casing for receiving said oscillating shaft.

6. The oscillatory saw of claim 5 wherein said drive rod has a second cylindrical bearing surface therein, and further comprising:
    a connecting shaft rotatably located within said second cylindrical bearing surface of said drive rod and fixedly attached to said crank for connecting said drive rod and said crank.

7. The oscillatory saw of claim 6 wherein said casing is filled with a lubricating fluid.

8. A high-speed oscillatory saw for cutting plaster casts or bone, and the like, comprising:
    a casing with bearing surfaces located therein filled with a lubricating fluid;
    a rotary shaft to be driven by a motor means mounted for rotation in at least one bearing surface of said casing;
    an oscillatory shaft mounted for circumferential oscillatory motion in at least one bearing surface of said casing, parallel to said rotary shaft;
    a cylindrical cam keyed to said rotary shaft for rotation therewith;
    a crank pinned to said oscillatory shaft;
    a drive rod having a first cylindrical bearing surface therein for receiving said cylindrical cam for rotation therewith and imparting an oscillatory motion to said crank; and
    a saw blade removably attached to an end of said oscillatory shaft.

9. The oscillatory saw of claim 8 wherein said casing is filled with a lubricating fluid.

10. The oscillatory saw of claim 9 wherein said drive rod has a second cylindrical bearing surface thereon, and further comprising:
    a connecting shaft rotatably located within said second cylindrical bearing surface of said drive rod and fixedly attached to said crank for connecting said drive rod and said crank.

* * * * *